United States Patent [19]

Booth et al.

[11] Patent Number: 5,662,607
[45] Date of Patent: Sep. 2, 1997

[54] CARDIOPLEGIA CATHETER WITH ELONGATED CUFF

[75] Inventors: William M. Booth, Paw Paw, Mich.; Jean-Aubert Barra, Brest, France

[73] Assignee: Medtronic, Inc., Minneapolis, Minn.

[21] Appl. No.: 475,072

[22] Filed: Jun. 7, 1995

Related U.S. Application Data

[63] Continuation of Ser. No. 146,293, Oct. 29, 1993, Pat. No. 5,505,698.

[51] Int. Cl.⁶ ............................................. A61M 29/00
[52] U.S. Cl. ............................................. 604/96; 604/104
[58] Field of Search ........................... 604/96, 101, 104; 606/192, 194

[56] References Cited

U.S. PATENT DOCUMENTS

| | | | |
|---|---|---|---|
| 4,019,515 | 4/1977 | Kornblum et al. | 604/101 |
| 5,021,045 | 6/1991 | Buckberg et al. | 604/53 |
| 5,042,976 | 8/1991 | Ishitsu et al. | 604/96 |
| 5,078,681 | 1/1992 | Kawashima | 604/53 |
| 5,197,952 | 3/1993 | Marcadis et al. | 604/96 |
| 5,250,025 | 10/1993 | Sosnowski et al. | 604/51 |

*Primary Examiner*—Corrine M. McDermott
*Attorney, Agent, or Firm*—Varnum, Riddering, Schmidt & Howlett LLP

[57] ABSTRACT

A catheter for supplying liquid to the coronary sinus in a perfusion procedure comprising a tubular catheter body having an interior lumen, a proximal end, and a distal end; and an inflatable cuff (balloon) adjacent the distal end of the catheter. The cuff has a proximal end and a distal end, each of which encircle the catheter body and hermetically seal thereto. The cuff further comprises an elongated central section having a length of at least 1 inch. When the inflated cuff is positioned a sufficient distance into the coronary sinus to firmly retain the cuff therein, it blocks the left coronary vein where it meets the coronary sinus. Further, the cuff can comprise end panels defined between the central section and the proximal and distal cuff ends. The end panels have a shape which allows for flexure between the central section and the cuffs proximal and distal ends.

2 Claims, 8 Drawing Sheets

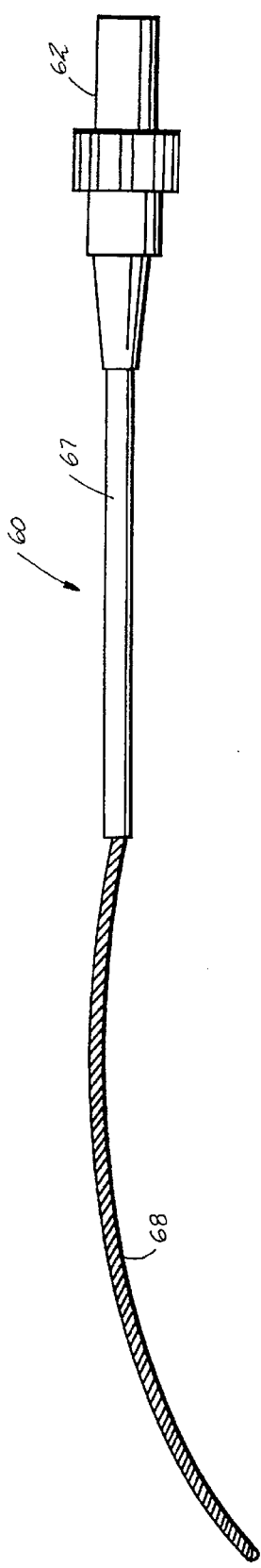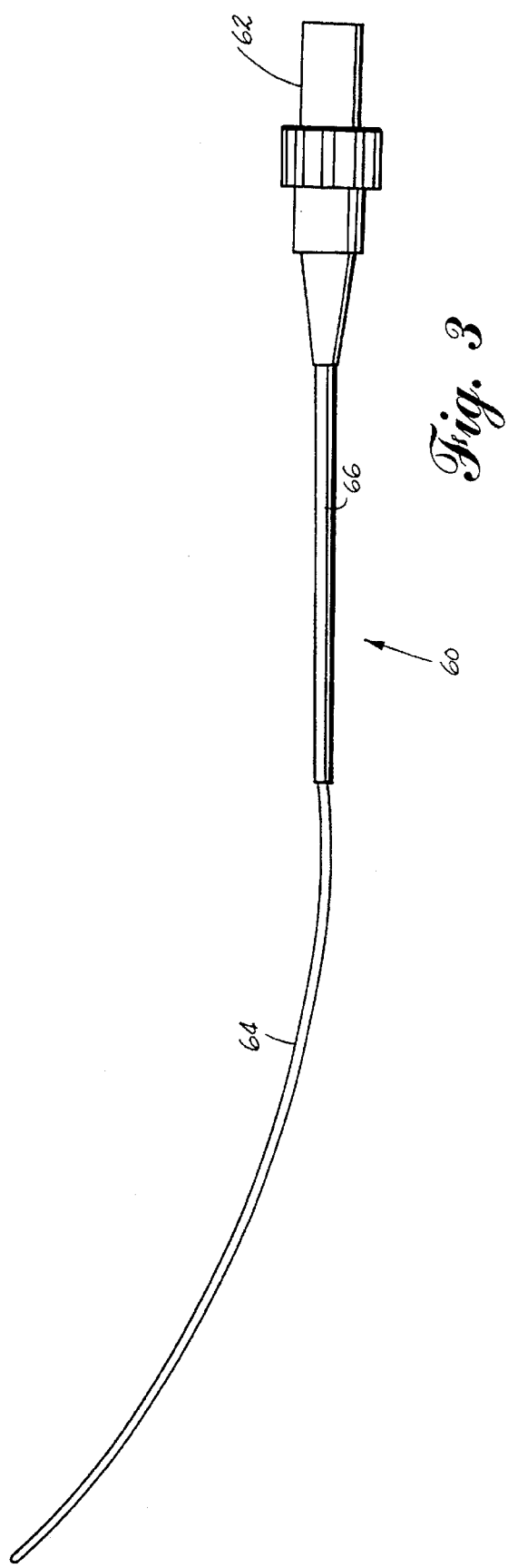

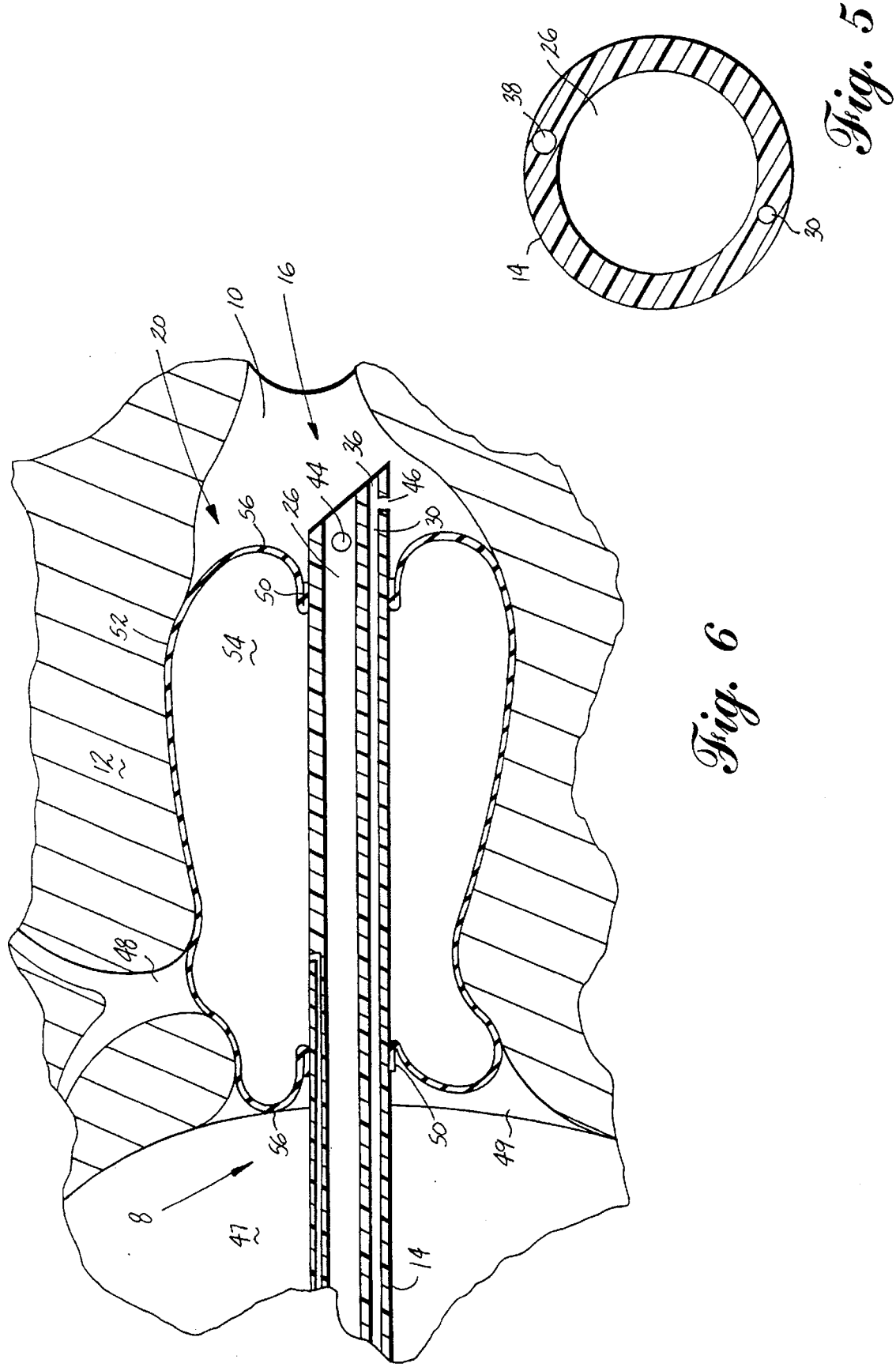

CARDIOPLEGIA CATHETER WITH ELONGATED CUFF

This is a continuation of application Ser. No. 08/146,293 filed Oct. 29, 1993 now U.S. Pat. No. 5,505,698.

BACKGROUND OF THE INVENTION

1. Field of the Invention

This invention relates to cardioplegia catheters having elongated inflatable cuffs for improved cardioplegia distribution.

2. Description of Related Art

Since the early days of cardiac surgery, it has been recognized that in order to provide the optimum surgical conditions when operating on the heart, it is necessary to interrupt the normal operation of the heart. For obvious reasons, an arrested, flaccid heart is preferred during cardiac surgical procedures over a beating heart with blood flowing through it. Thus, in order to be able to efficiently perform cardiac surgery, it is often necessary to use cardiopulmonary-bypass techniques and to isolate the heart from its life-giving blood supply.

The heart is divided into a left and a right half. The right side of the heart is smaller and pumps deoxygenated blood returning from the body into the lungs. The left side of the heart performs the bulk of the work, and pumps oxygenated blood from the lungs to the rest of the body. Each side of the heart has an upper chamber, called an atrium, and a lower chamber, called a ventricle. The atrial chambers accumulate blood and supply it to the ventricular chambers, which actually do the pumping work.

The ventricular chambers operate by expanding and drawing blood in from the atriums, then contracting and forcing the blood out. Inlet and outlet check valves keep the blood moving in the right direction. The right atrium and right ventricle are connected through the tricuspid valve. The left atrium and left ventricle are connected through the mitral valve. The right ventricle pumps blood out through the pulmonary valve, and the left ventricle through the aortic valve.

Deoxygenated blood returns from the body to the heart by means of the vena cava into the right atrium. During the heart's diastole (expansion), the blood is drawn through the tricuspid valve into the right ventricle. During the heart's systole (contraction), blood is forced from the right ventricle, into the pulmonary artery and on into the lungs to be oxygenate. Oxygenated blood returns from the lungs by means of the pulmonary vein, and enters the left atrium. During the heart's systole, the blood is forced out of the left ventricle, through the aortic valve and into the aorta, from whence it branches off to serve all areas of the body including the heart itself.

The blood supply which serves the heart muscle with oxygenated blood originates from two openings, called coronary ostia, in the aorta near the aortic valve. From the coronary ostia, the blood flows through the coronary arteries, and branches off into a myriad of tiny capillaries to provide oxygenated blood to all areas of the heart muscle. Approximately 80% of the blood entering the coronary arteries drains through veins into the coronary sinus vein, which in turn drains into the right atrium. The remaining blood drains by alternative passages into the heart's chambers, primarily the right atrium.

During cardiac surgery, the heart is isolated from the circulatory system and the patient is connected to a heart-lung machine which oxygenates and pumps blood. A venous catheter is inserted into the right atrium and drains blood returning from the body into the heart lung machine. An arterial cannula is inserted into the aorta, so that oxygenated blood from the heart-lung machine can be pumped back into the body. After these catheters are in place, the aorta is cross clamped between the arterial cannula and the heart, to prevent blood from flowing backwards into the heart. Cross clamping involves pinching the aorta closed with a clamp having elongate jaws which extend the full width of the aorta. The foregoing procedure provides blood to all areas of the body except the heart, because the aortic clamping prevents oxygenated blood from the heart-lung machine from entering the coronary arteries. Accordingly, some method must be provided for preventing degradation of the heart tissue during the surgery.

One of the early methods utilized to protect the heart muscle during surgery was normothermic (body temperature) perfusion of the empty beating heart. This method was utilized in an effort to maintain the heart, as much as possible, in normal conditions during surgery. Although this procedure eliminated the problem of blood flow, dissection and suturing were still difficult to perform because of the firmness and the beating of the heart. Additionally, it was found that a significant amount of damage still occurred to the heart muscle when this procedure was utilized.

A second method developed to protect the myocardium was intermittent cardiac ischemia (stoppage of blood flow to the heart muscle) with moderate hypothermia. This method requires that the entire body be cooled to a temperature from 28° C. to 32° C., thus slowing all bodily functions, including those of the heart. The heart is electrically stimulated to induce fibrillation (mild fluttering) before aortic cross-clamping to stop the beating. The surgeon can then operate for approximately 15–25 minutes, after which time the heartbeat is necessarily resumed for 3–5 minutes. This procedure proved to be an inefficient method for performing operations and had many attendant dangers, including fibrillation of the heart.

A third method which has been utilized is profound hypothermic cardiac ischemia. This method requires that the temperature of the heart be lowered to about 22° C. by the infusion of a cooled perfusate and/or by filling the pericardium (chest cavity containing the heart) with cold saline solution. One of the major disadvantages of this technique is that the heart continues to fibrillate, exhausting the heart-stored energy. As a result, the heart becomes acidotic, which over time causes irreversible muscle damage.

Currently, the most common method to preserve the myocardium during surgery is the infusion of a cold cardioplegic fluid to both cool the heart and stop it from beating. After the initial infusion, the heart is reperfused approximately every 30 minutes to maintain the cool, dormant state of the heart. Alternatively, a continuous flow of cardioplegic solution may be provided.

The use of cardioplegia, which literally means "heart stop," to protect the myocardium has proven the most advantageous method of those used to date. Cardioplegia solution may be administered in an antegrade manner (through arteries in the normal direction of blood flow), in a retrograde manner (through veins opposite the normal blood flow direction), or in a combination of retrograde and antegrade administration. Cardioplegic solutions, typically containing potassium, magnesium, procaine or a hypocalcemic solution, stop the heart by interfering with the heart's capacity to conduct the natural electric signals which tell it to beat.

In normal antegrade cardioplegia, a single needle is inserted into the aorta beneath the cross-clamp, and the cardioplegic solution is administered therethrough. The cardioplegic solution flows through the coronary arteries in the normal blood flow direction. Care must be taken to avoid mechanical injury to the coronary ostia which could produce the serious complications of coronary ostial stenosis (i.e., constricting of the coronary ostia). Ostial stenosis requires reparative surgery and can be quite hazardous due to obstruction of the coronary arteries. Moreover, it is a nuisance to have perfusion catheters present within the limited operative field during aortic valve replacement.

Retrograde cardioplegia is conventionally administered by inserting a balloon catheter into the coronary sinus, inflating the balloon, and perfusing the cardioplegic solution backwards through the coronary veins. Typically, catheters for retrograde coronary sinus perfusion (RCSP) may contain either a manually inflating, or auto-inflating balloon or cuff. A manually inflating cuff is filled through an inflation lumen, either attached to the outer surface of the cannula body, or integral to the cannula body. Typically, a syringe supplies the inflation fluid.

An auto-inflating cuff is filled by a flow of cardioplegic solution. Several methods are used to fill the auto-inflating cuff with cardioplegic solution, but all rely on the principle of a flow restriction downstream of the cuff to provide a back pressure for filling the cuff. In one design, the infusion lumen is plugged; the cuff has one or more inlets from the infusion lumen upstream of the plug and one or more outlets to the infusion lumen downstream of the plug. The combined surface area of the cuff outlets is less than the combined surface area of the cuff inlets, thereby providing sufficient back pressure to inflate the cuff. In this design, all of the cardioplegic solution flows through the interior of the cuff.

Because the coronary sinus is susceptible to damage from high pressures, some form of pressure monitoring should be employed during RCSP. Typically, a separate pressure lumen, either integral with the catheter body, or external to the catheter body, is provided. One or more openings are typically provided at or near the distal end of the cannula, so that the pressure lumen is in communication with the coronary sinus for accurate pressure monitoring. A separate opening, in communication with the infusion lumen, is sometimes provided as a security feature in case the primary openings to the coronary sinus become occluded.

RCSP offers several advantages over antegrade cardioplegia delivery. It avoids arterial ostial stenosis, there is no need to interrupt surgery for re-infusion, it allows prolonged cardioplegia delivery due to the low flow rates, and provides good uniformity of cardioplegia distribution throughout the heart. Menaschè, P. and Piwnica, A. H., "Retrograde Coronary Sinus Perfusion," *Roberts Textbook of Myocardial Protection in Thoracic Surgery*, Chap. 15, pp. 251–262 (1987).

One of the drawbacks of RCSP is a lower flow to the veins serving the right ventricle and atrium. While the coronary sinus drains a majority of the heart's blood supply, the remainder goes through alternative blood vessels, termed the arteriosinusoidal and thebesian vessels, directly into the cardiac chambers. Typically, these alternative systems serve the right ventricle and atrium. Thus, these areas of the heart will not receive as much cardioplegic solution during retrograde administration. An additional mechanical limitation arises from several small veins, from the right side of the heart, emptying into the coronary sinus as close as 0.5 cm. to the coronary sinus ostium. Id.

Of primary concern is the left coronary vein, a relatively large vein which drains into the coronary sinus adjacent its ostium. To ensure adequate retention of the inflated cuff within the coronary sinus, the cuff must generally be placed into the coronary sinus at a point beyond where the left coronary vein enters the coronary sinus. The left coronary vein is thus left open to the right atrium. The arterial and venous systems serving the heart rapidly branch into small capillaries through which there are many interconnections. There is concern that the left coronary vein may act as a shunt which allows cardioplegia fluid entering the coronary sinus at a pressure of 40 mm Hg to seek the atmospheric pressure of the right atrium through the left coronary veins, thus bypassing more distal regions of the coronary venous system.

As previously described, dislodgement of the catheter from its position within the coronary sinus is a further concern. Typically, as the cuff is inflated to a higher pressure to obtain a higher retentive force, it becomes more rigid and loses elasticity in the axial direction. Axial forces accidentally applied to the catheter during the operation are not absorbed by the cuff but are transmitted directly to the wall of the cuff in contact with the coronary sinus. This can result in the cuff becoming dislodged from its position within the coronary sinus.

The catheter of the present invention employs an inflatable cuff which overcomes these problems by purposely occluding the left coronary vein during the perfusion procedure to prevent cardioplegia fluid from "leaking" out of the coronary sinus through the left coronary vein. Additionally the design of the cuff allows it to absorb axial forces applied to the catheter to inhibit dislodgement of the catheter from the coronary sinus.

SUMMARY OF THE INVENTION

In its broader aspects, the invention comprises a catheter for supplying liquid to the coronary sinus in a perfusion procedure. The catheter comprises a tubular catheter body having an interior lumen, a proximal end, and a distal end. An inflatable cuff adjacent to the distal end of the catheter has a proximal end and a distal end. The proximal and distal ends of the cuff encircle the catheter body and hermetically seal thereto. The cuff further comprises an elongated central section disposed between the ends thereof and having a length of at least a magnitude whereby when the cuff is inserted into the coronary sinus a sufficient distance that the cuff will be securely retained within the coronary sinus, and when the cuff is then inflated, the cuff will block the left coronary vein where it intersects the coronary sinus. Preferably, the length of the central section along the catheter body is at least one inch. Also, the cuff preferably comprises elastic silicone material.

In one of the preferred embodiments of the invention, the cuff comprises a tubular section of elastic material, and the material of the cuff is relaxed in the axial direction when the cuff is deflated. Alternatively, the material of the cuff can be compressed in the axial direction when the cuff is deflated.

In a further aspect of the invention, the cuff includes a pair of end panels. A first one of the end panels is defined between the proximal end of the cuff and the central section thereof, and a second one of the end panels is defined between the distal end of the cuff and the central section thereof. Each of the end panels assumes a configuration upon inflation of the cuff which allows flexure between the central section and the respective end of the cuff. Preferably, the end panels assume an S-shape in cross section upon inflation of the cuff.

A further aspect of the invention comprises a stop on the catheter body, positioned a predetermined distance proximally from the cuff, whereby as the cuff is inserted into the coronary sinus, the stop abuts the heart muscle surrounding the opening of the coronary sinus, and the cuff is thereby correctly positioned within the coronary sinus. The stop can be expandable radially outwardly from the catheter body. Preferably, the stop is formed of flexible material and has a resting configuration wherein the stop extends radially outwardly from the catheter body.

In one aspect of the invention, a thread attaches to a radially outward portion of the stop. The thread passes through a lumen in the catheter body, whereby upon application of tension to the thread, the stop is drawn into a configuration wherein the stop extends radially outwardly from the catheter body a distance smaller than in the resting configuration thereof. Alternatively, the stop comprises a second inflatable cuff.

A further aspect of the invention comprises a method for attaching a cuff to a catheter body. The catheter body comprises a distal end, a proximal end, an inflation lumen and an infusion lumen. The inflation lumen exits the catheter body proximally of the distal end, and the cuff comprises a tubular section of elastic material. The method includes the following steps. Coaxially receive the catheter body within the tubular section of elastic material, with the exit of the inflation lumen within the tubular section of elastic material. Adhere one end portion of the tubular section of elastic material to the catheter body to form a hermetic seal between the end portion and the catheter body. Place the tubular section of elastic material into a relaxed state in the axial direction whereby it is neither under tension, nor compression in the axial direction. Adhere an opposite end portion of the tubular section to the catheter body to form a hermetic seal therewith. The cuff is in a relaxed condition in the axial direction when deflated, and upon introduction of an inflation fluid through the inflation lumen into a space formed between the cuff and the catheter body, the cuff expands radially outwardly from the catheter body and is flexible in the axial direction.

A method according to the invention for the retrograde administration of a cardioplegic solution into the into the coronary sinus of the heart comprises the following steps. Insert a catheter through a small incision in the right atrium of the heart. The catheter comprises a tubular catheter body having an interior lumen, a proximal end, and a distal end. An inflatable cuff adjacent to the distal end of the catheter has a proximal end and a distal end. The proximal and distal ends of the cuff encircle the catheter body and hermetically seal thereto. Further, the cuff comprises an elongated central section. Manipulate the catheter to position the distal end of the catheter, and the cuff, within the coronary sinus vein of the heart, so that upon inflation, the cuff will be in contact with the walls of the coronary sinus, and the cuff will occlude the left coronary vein, and other veins draining into the coronary sinus vein adjacent its opening in the heart's right atrium. Inflate the balloon and inject cardioplegic solution through the cannula and into the coronary sinus. The occlusion of the left coronary vein prevents cardioplegic solution from leaking out of the coronary sinus proximal of the cuff, through a network of blood vessels between the coronary sinus distal of the cuff and the left coronary vein.

These, and other objects, features and advantages of the invention will be apparent from the ensuing description in conjunction with the accompanying drawings.

BRIEF DESCRIPTION OF THE DRAWINGS

The invention will now be described with reference to the drawings wherein:

FIG. 3 is a side elevational view of a stylet for the catheter of FIG. 1;

FIG. 4 is a side elevational view of an alternative stylet for the catheter of FIG. 1;

FIG. 5 is a sectional view of the Catheter taken along lines 5—5 of FIG. 2;

FIG. 6 is a detailed sectional elevational view of the cuff of the catheter of FIG. 1;

DESCRIPTION

Figure 1:
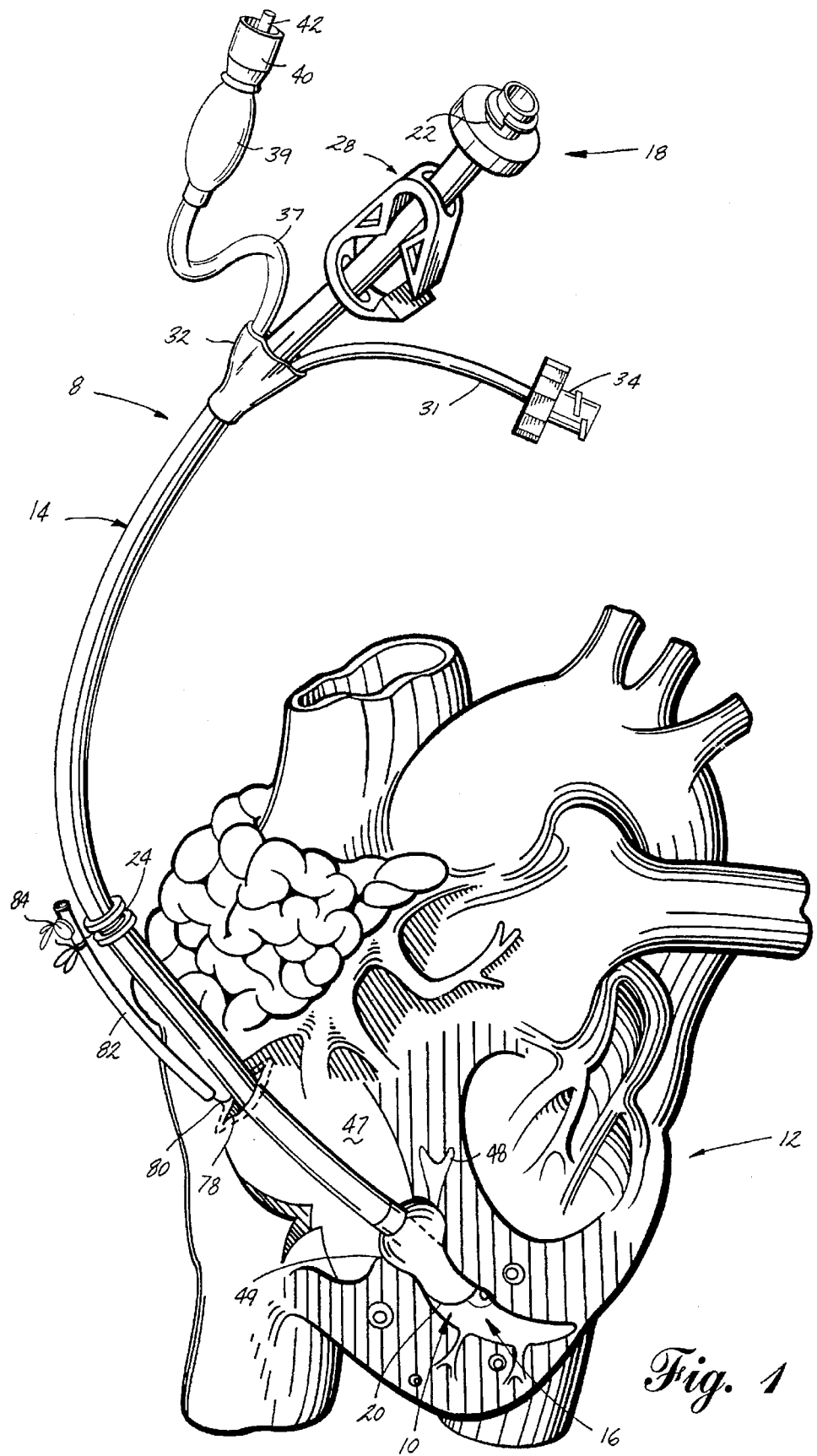
FIG. 1 is a partial sectional side elevational view of an inflatable cuff catheter according to the invention, inserted into a coronary sinus vein.

Referring now the drawings and to FIG. 1 in particular, a catheter 8 for the introduction of fluid to a body organ is shown positioned in the coronary sinus vein 10 of a heart 12. The catheter 8 comprises a catheter body 14, having a distal end 16 and a proximal end 18. An inflatable balloon comprising a cuff 20 surrounds and attaches to the catheter body 14 near its distal end 16, and a locking female luer 22 attaches at its proximal end 18. A suture ring 24 slidably mounts on the catheter body 14 and serves as an aid in securing attachment of the catheter 8 to the heart 12, as will be more fully described hereinafter.

Figure 2:
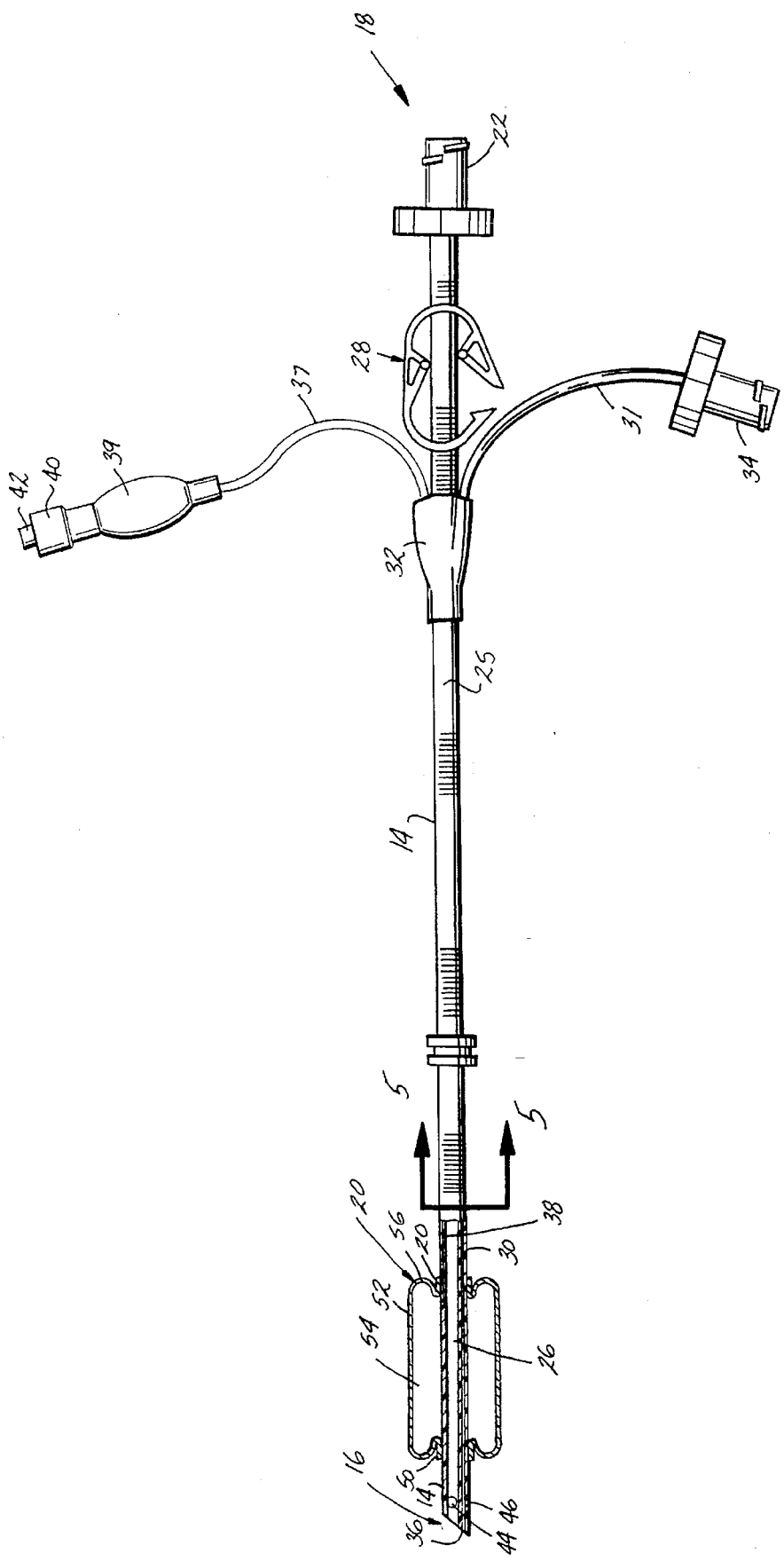
FIG. 2 is a side elevational view of the catheter of FIG. 1.

Turning to FIG. 2, the catheter body 14 is preferably formed of a flexible plastic material, such as silicone, suitable for introduction into the human body. As seen in section, the catheter body 14 is generally tubular, cross forming an infusion lumen 26 therethrough (see FIG. 5). The conventional locking female luer 22 connects the catheter body 14 to a source of cardioplegia solution (not shown). A clamping member 28 of conventional design mounts on the catheter body 14 adjacent and distal to the locking female luer 22 for squeezing the catheter body 14 to occlude the infusion lumen 26. A coiled wire 25, incorporated into the catheter body 14 distal of the clamp 28, resists collapse or kinking of the catheter body 14.

A separate pressure monitoring lumen 30, running over substantially the entire length of the catheter body 14, provides pressure monitoring capability. The pressure monitoring lumen 30 is preferably integrally molded into the catheter body 14 (See also FIG. 5), except for its proximal end, which exits near the proximal end 18 of the catheter body 14 to terminate in a pressure monitoring line 31. A strain relief sleeve 32 made of an elastic material surrounds the catheter body 14 and pressure monitoring line 31 at the point the pressure monitoring lumen 30 exits the catheter body 14. An adhesive can be used to help seal the sleeve 32 to the catheter body 14 and pressure monitoring line 31.

A locking female luer 34 mounts on the proximal end of the pressure monitoring line 31 and connects to a pressure monitoring device (not shown). The connector hub 34 may incorporate an integral three way valve (not shown) so that the pressure monitoring line 31 can simultaneously connect to alternatively selectable pressure monitoring devices. The pressure monitoring lumen 30 extends to the distal end 16 of the catheter 8 so that the pressure monitoring device is in pressure communication with the inside of the coronary sinus 10 (FIG. 1).

A separate inflation lumen 38, running over substantially the entire length of the catheter body 14, provides a passageway for fluid used to inflate the cuff 20. The inflation lumen 38 is preferably integrally molded into the catheter body 14 (see also FIG. 5), except for its proximal end, which exits the catheter body 14 at the strain relief sleeve 32, and which comprises a separate tubular inflation line 37. A conventional pilot balloon 39, and a one way valve 40 with a female slip luer 42 mount on the proximal end of the inflation line 37.

The distal end of the inflation lumen 38 terminates inside of the cuff 20, so that fluid, such as air, can pass through the inflation lumen 38 to inflate the cuff 20. The one way valve 40 prevents the inflation fluid from escaping the cuff 20, and thus keeps the cuff 20 inflated, until the one way valve 40 is manually released, whereupon the inflation fluid flows out of the cuff 20 through the inflation lumen 38, and past the open one way valve 40.

At the distal end of the catheter 16, one or more auxiliary discharge apertures 44 may be provided. The auxiliary discharge apertures 44 are located distal of the cuff 20, and lead from interior of the infusion lumen 26, radially through the catheter body 14. Therefore, if for some reason the distal end of the catheter 16 were to become blocked or occluded in any manner, the auxiliary discharge aperture 44 would discharge the flow of cardioplegic fluid into the coronary sinus 10. Also, an auxiliary pressure monitoring passage 46 may be provided adjacent to the distal end of the catheter 16, extending radially outwardly from the pressure monitoring lumen 30 through the catheter body 14. Alternatively, the auxiliary pressure monitoring passage 46 may extend radially inwardly from the pressure monitoring lumen 30 into the infusion lumen 26, immediately adjacent the catheter distal end 10. In either case, if the distal end of the pressure monitoring lumen 30, at the distal end of the catheter 16, should become occluded for any reason, accurate pressure readings of the pressure within the coronary sinus 10 could still be obtained through the auxiliary pressure monitoring passage 46.

Returning to FIG. 1, and also to FIG. 6, it can be seen that the coronary sinus 10 drains into the right atrium 47 of the heart 12 and that one of the major blood vessels draining a large area of the heart and entering the coronary sinus 10, the left coronary vein 48, enters the coronary sinus 10 immediately adjacent the ostium 49 (opening) of the coronary sinus 10 into the right atrium 47.

In a catheter employing a conventional round or pear-shaped cuff; the cuff must be inserted well into the coronary sinus 10 to ensure adequate retention within the coronary sinus 10. This often means that the cuff would be inserted past the point at which the left coronary vein 48 enters the coronary sinus 10. Thus, the left coronary vein 48 would not be adequately perfused. Also, the left coronary vein 48 would be open to the right atrium 47 of the heart through the coronary sinus 10.

Some researchers believe that the open left coronary vein 48 allows cardioplegia fluid being pumped into the coronary sinus 10 to bypass a portion of the circulatory system of the heart and "leak" back into the coronary sinus 10 proximal of the cuff, through the left coronary vein 48. The cardioplegic fluid being pumped into the coronary sinus 10 will seek the path of least resistance. In this case, it is believed that the path of least resistance is not through the veins, into the capillaries and finally out through the arteries to the aorta. Instead, the path of least resistance for the region of the heart adjacent the left coronary vein 48 is through a network of tiny vessels interconnecting the left coronary vein 48 and the coronary sinus 10. The bypass thus created effectively diminishes the flow to the region of the heart served by the left coronary vein 48.

Prior designs have attempted to ensure that all veins draining into the coronary sinus 10 receive adequate perfusion by placing an inflated cuff into the coronary sinus 10 as close as possible to its ostium 49 into the right atrium 47. However, bodily fluids tend to lubricate the walls of the coronary sinus 10 making them slippery. Additionally, the coronary sinus 10 is elastic and expands in the direction of its ostium 49, so that it tends to expel, rather than retain, objects placed within it. Thus, placing and retaining a balloon in the coronary sinus 10, distal of the veins entering the coronary sinus adjacent its ostium remains a difficult task.

An alternative solution is proposed. The cuff 20, of the present invention, overcomes these limitations through its elongated shape which blocks the junction of the left coronary vein 48 with the coronary sinus 10 to prevent cardioplegia fluid from bypassing the region of the heart 12 served by the left coronary vein 48. Whereas typical prior manually inflatable cuffs have an axial length of about ⅜ inch, the elongated cuff 20 of the present invention is preferably 1⅓ inches long. Therefore, the distal end of the catheter 16, and the cuff 20, may be inserted a substantial distance into the coronary sinus 10 for good retention of the cuff 20 within the coronary sinus 10, while still blocking the juncture between the left coronary vein 48 and the coronary sinus 10. The cuff 20 thus prevents cardioplegia fluid from draining through the left coronary vein 48 back into the coronary sinus 10 proximal of the cuff 20. Blocking the left coronary vein 48 in this fashion, has the potential for forcing the cardioplegia fluid out into the more distal regions of the circulatory system of the heart 12.

The cuff 20 comprises an elongated, cylindrical sleeve of elastomeric silicone, which is placed over the catheter body 14. At each of its ends, approximately 0.1 inches of the cuff 20 is bonded to the catheter body 14 using a suitable adhesive, forming bond areas 50. A central section 52, between the bond areas, expands when pressurized fluid is applied to the inflation lumen 38, forming an interior cuff space 54 between the cuff 20 and the catheter body 14.

To form a rigid, well shaped balloon upon inflation, prior inflatable cuffs are prestressed prior to being affixed to the catheter body. Typically, one end of the cuff is bonded to the catheter body at the bond area, the cuff is stretched axially, and then the opposite end of the cuff is bonded to the catheter body. The cuff 20 of the present invention, is not prestressed prior to bonding to the catheter body 14. It is bonded to the catheter body 14 at its bond areas 50 with the cuff 20 in its relaxed, or unstretched shape. Upon inflation, end sections 56 of the cuff 20 adjacent the bond areas 50 expand and extend axially beyond the bond areas 50. In effect, the cuff 20 folds back over itself so that the end sections 56 assume an S-shape upon inflation.

The S-shape of the end sections 56 allows them to flex in the longitudinal direction of the catheter 8. The cuff central section 52 engages the wall of the coronary sinus 10. Axial forces applied to the catheter body 14 are absorbed first by the flexible end sections 56, allowing the catheter body 14 to move axially relative to cuff central section 52, which remains fixed within the coronary sinus 10.

The concept is also applicable to pediatric catheters. Whereas a typical adult catheter has a 15 French diameter (1 French=approximately ⅓ mm), a pediatric catheter may have a diameter of 6 French or less. Present manually inflated 6 French pediatric catheters have approximately ⅜" long cuffs comprising ¹⁄₁₆" long bond areas at each end with a ¼" long central section. A pediatric catheter 8 according to the invention preferably has a ¾" long cuff 20 comprising ¹⁄₁₆" long bond areas 50 and a ⅝" long central section 52.

The catheter body 14 is flexible and requires stiffening for proper insertion into the heart's coronary sinus vein 10. Turning also to FIG. 3, a stiff stylet 60 provides the necessary rigidity, and inserts coaxially into the catheter's infusion lumen 26 through the infusion lumen locking female luer 22 at the proximal end 18 of the catheter 8. The stylet 60 is removed from the catheter body 14 after the catheter 10 is properly positioned in the coronary sinus 10. As shown in FIG. 3, the styler 60 comprises a handle 62, and an elongated malleable wire 64 extending therefrom. A relatively rigid, although also malleable, sheath 66 extends from the handle 62 and coaxially receives the proximal third of the malleable wire 64. Addition of the sheath 66 is optional, however, it provides added rigidity over the proximal portion of the stylet 60. Thus, it is malleable for forming, yet rigid for proper stiffening of the catheter 10.

The surgeon typically forms the malleable wire 64 into a curved shape, similar to the curve of a hockey stick, with the stylet 60 received within the catheter body 14. Alternatively, the wire 64 may be manufactured with a preformed appropriate curve, which may be further customized by the individual surgeon. FIG. 4 shows an alternative stylet 60 having a malleable helical spring 68, in place of the malleable wire 64 of the stylet 60 of FIG. 3, and a sheath 67.

Returning to FIG. 1, the catheter 8 according to the invention, is well suited for supplying cardioplegia solution to the heart muscle 12 during a surgical procedure. First, the surgeon places a small atriotomy (incision into the heart's atrium) 78 and purse string suture 80 into the right atrial wall of the heart 12, leaving the free ends of the suture 80 to extend through a tourniquet tube 82. The styler 60 (FIG. 3) is bent into a suitable hockey stick shaped curve and placed inside the infusion lumen 26 of the catheter 8 to provide rigidity.

The distal end 16 of the catheter 8, with the stylet 60 in place, is introduced into the right atrium 47 of the heart 12, through the atriotomy 78 and purse string suture 80 in the right atrial wall of the heart 12. The catheter body 14 is inserted into the coronary sinus 10 through its ostium (opening) 49. The cuff 20 is then inflated through the introduction of an inflation fluid, such as air, or saline solution through the inflation lumen 38. Typically a syringe (not shown), attached to the female slip luer 42, supplies the inflation fluid. The one way valve 40 maintains the inflation pressure within the cuff 20. The purse string 80 is tightened, and a clamp 84 on the tourniquet tube 82 is closed to hold the ends of the purse string suture 80. The tourniquet 82 can be is attached to the suture ring 24 on the catheter body 14 with additional suture material. The pressure monitoring lumen luer 34 and infusion lumen luer 22 are connected to their respective pressure monitor and cardioplegia sources and the lumens are purged of air in the standard fashion.

Once the catheter 8 is properly positioned within the coronary sinus 10 and connected to the pressure monitoring and cardioplegia supplying equipment (not shown), a suitable cardioplegia solution is introduced into the infusion lumen 26 through its proximal end. The pressurized solution flows into the heart 12 tissue through the veins which normally empty into the coronary sinus 10 and arrests beating of the heart 12. Depending on the composition of the solution employed, the solution can also provide necessary oxygen to the heart tissue to prevent damage thereto. Pressure monitoring equipment (not shown) connected to the pressure monitoring lumen 30 measures the pressure of the cardioplegia solution within the coronary sinus 16.

The cuff 20 serves two distinct functions in a cardioplegia perfusion process. First, the cuff 20 substantially fills the sinus ostium 49 thereby sealing the coronary sinus 10 from the right atrium of the heart 12. The pressurized cardioplegia solution introduced into the coronary sinus 10 through the catheter 8 is forced to flow backwards through the coronary sinus 10 into the veins which typically drain into the coronary sinus 10, and from there through the capillaries which serve the heart 12. Second, the cuff 20 engages the inside circumference of the coronary sinus 10 and sinus ostium 49 and retains the catheter 8 in place during the cardioplegia perfusion process. As previously discussed, the length of the cuff 20 allows it to be placed deeply inside the coronary sinus for high retention, while also sealing the junction of the left coronary vein 48 with the coronary sinus 10.

The stop 100 shown comprises a truncated hollow cone which is bonded to the catheter body 14a. However, any suitable means for abutting the heart 12 adjacent the coronary sinus ostium 49 may be so employed. Preferably, the stop 100 is expandable from a low profile configuration abutting the catheter body 14a, to a configuration where the stop extends outwardly radially from the catheter body 14a. The low profile configuration of the stop 100 aids in passing the stop through the small atriotomy 78 (FIG. 1).

Figure 7:
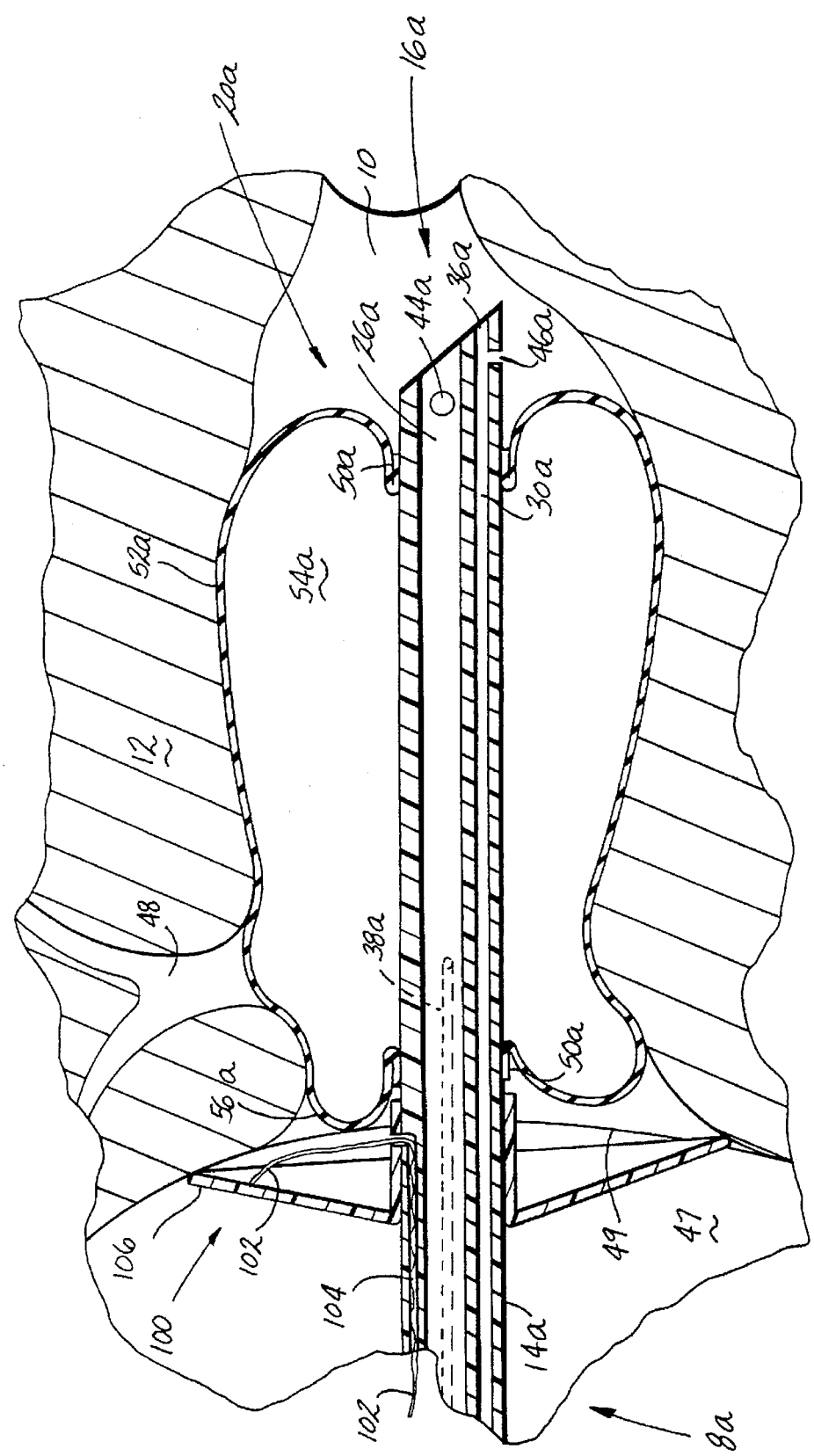
FIG. 7 is a detailed sectional elevational view of a second embodiment of a catheter according to the invention, having a folding stop for proper positioning of the catheter within the coronary sinus.

In the stop 100 shown in FIG. 7, the material of the stop 100 is flexible, and in its relaxed position, extends outwardly radially from the catheter body 14a. The stop 100 may be manually folded into a low profile configuration for insertion through the atriotomy 78, or may be provided with a means for contracting the stop 100 into a low profile configuration. Such a means may comprise one or more threads 102 passed through a third catheter lumen 104 terminating adjacent the stop 100. The threads 102 attach at one end to a radial outward portion 106 of the stop 100 so that tension on the threads tend to pull the stop 100 toward the catheter body 14a and into a low profile configuration.

Figure 8:
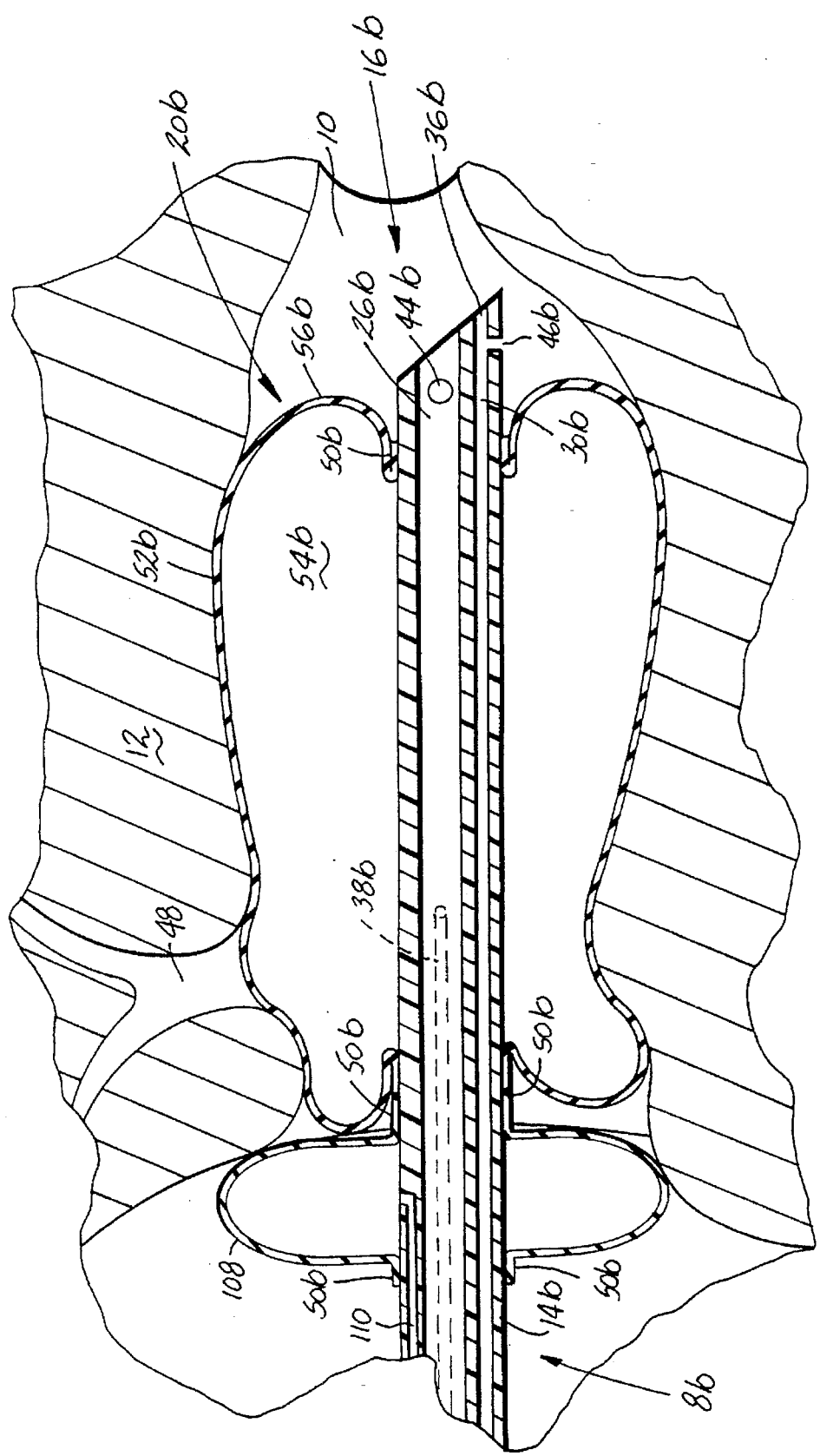
FIG. 8 is a detailed sectional elevational view of a third embodiment of a catheter according to the invention, having an inflatable stop for proper positioning of the catheter within the coronary sinus.

FIG. 8 illustrates a third embodiment of a catheter 8b according to the invention. Like parts are given like numerals, with the subscript "b". The catheter 8b is similar to catheter 8a, except that the stop 100 is replaced with an inflatable locating cuff 108. The locating cuff 108 affixes to the catheter body 14b similarly to the cuff 20b, as described with reference to cuff 29 above, but preferably takes a discoid shape upon inflation, as shown. A locating cuff inflation lumen 110 in the catheter body 14b provides fluid for inflating the locating cuff 108. The locating cuff 108 can be a separate cuff (not shown) from the main cuff 20b or can be formed by providing an intermediate bond area 50b between the distal and proximal bond areas 50b of the cuff 20, thereby dividing the tubular section of material forming the cuff 20 into the locating cuff 108 and the main cuff 20b.

In practice, the surgeon first inserts the catheter distal end 16b into the right atrium of the heart 47 and inflates the locating cuff 108. The surgeon then inserts the catheter distal end 16b and cuff 20b into the coronary sinus 10 until the locating cuff 108 abuts the wall of the right atrium at the coronary sinus ostium 49. Alternatively, the surgeon may wish to partially insert the catheter 8b into the coronary sinus 10 prior to inflating the locating cuff 108. In any event, the perfusion procedure proceeds from this point as described above with respect to the first embodiment.

Figure 9:
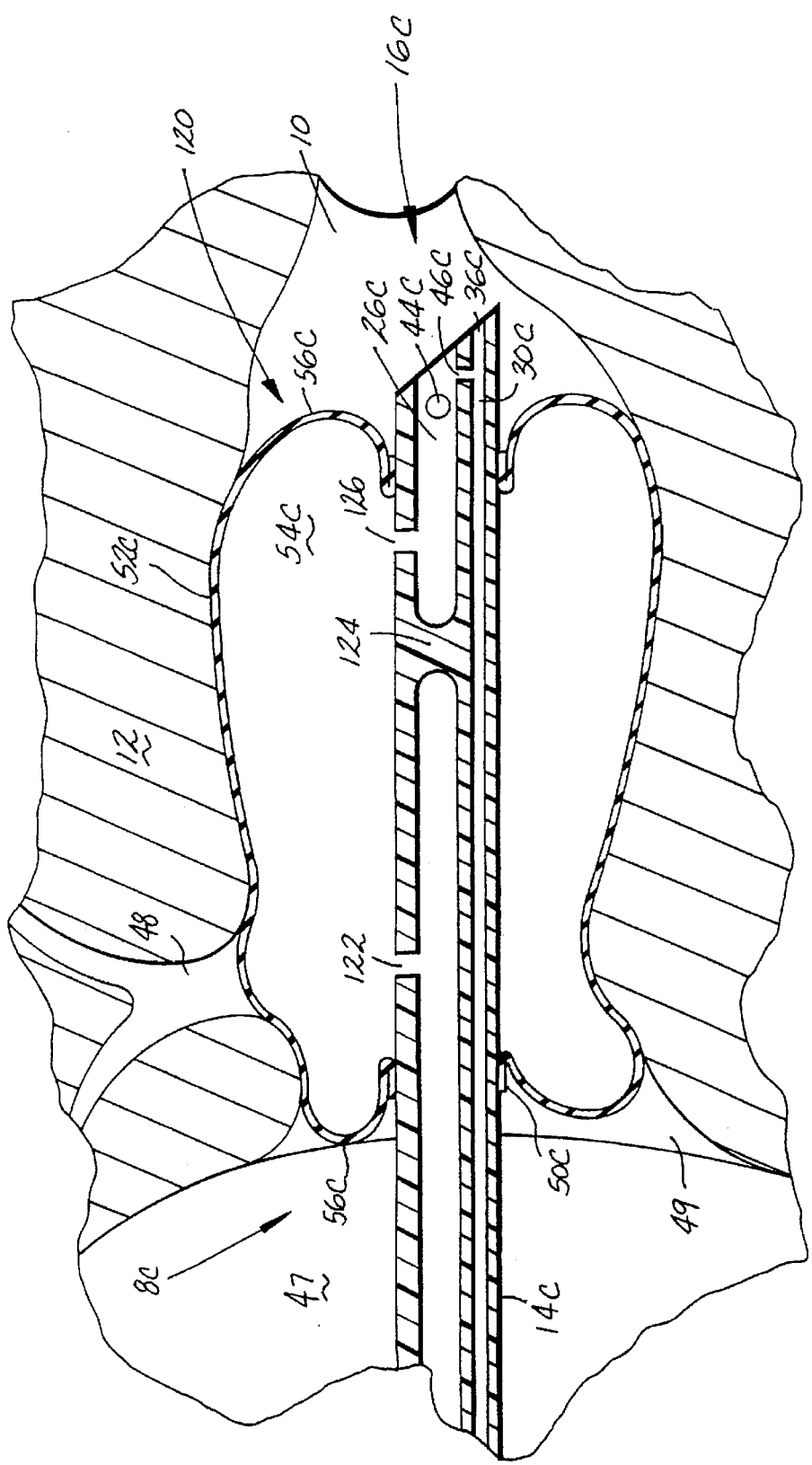
FIG. 9 is a sectional elevational view of a fourth embodiment of a catheter according to the invention, having a self-inflating cuff.

FIG. 9 illustrates a fourth embodiment of a catheter 8c according to the invention and, as in the second and third embodiments, like parts are given subscripted like numerals; in this case, "c." As opposed to the manually inflatable cuff 20 of the previous embodiments, the catheter 8c employs an auto-inflating cuff 120, which inflates under a back pressure caused by the flow of cardioplegia solution. The infusion lumen 26c communicates with the cuff interior 54c through at least one cuff inflation aperture 122. As pressurized fluid is forced through the infusion lumen 26c, it enters and inflates the auto-inflating cuff 120. The fluid also flows out of the catheter distal end 16c through the infusion lumen 26c. A plug 124 in the infusion lumen 26c forces all of the cardioplegia solution flowing through the infusion lumen 26c to enter the cuff interior 54c through the cuff inflation apertures 122.

The cardioplegia solution flows out of the cuff interior 54c, and returns into the infusion lumen 26c, through exit apertures 126, located distal of the plug 124. The aggregate cross-sectional area of the inflation apertures 122 exceeds the aggregate cross-sectional area of the exit apertures 126, thereby providing a positive pressure in the cuff interior 54c to keep the cuff 120 inflated during flow of the cardioplegia solution.

The auto-inflating cuff 120 is also preferably formed of silicone, but is relatively inelastic to ensure proper inflation under the low fluid pressure of the cardioplegia fluid. Note that the auxiliary pressure monitoring passage 46c extends between the pressure monitoring lumen 30c and the infusion lumen 26c at the catheter distal end 16c. Also, the auto-inflating cuff 120 may be used in conjunction with a manually inflatable locating cuff such as the cuff 108, or with other stop means. U.S. Pat. No. 5,197,952 to Marcadis et al., issued Mar. 30, 1993, incorporated herein by reference, more fully describes the design and operation of auto-inflating RSCP cuffs.

Figure 10:
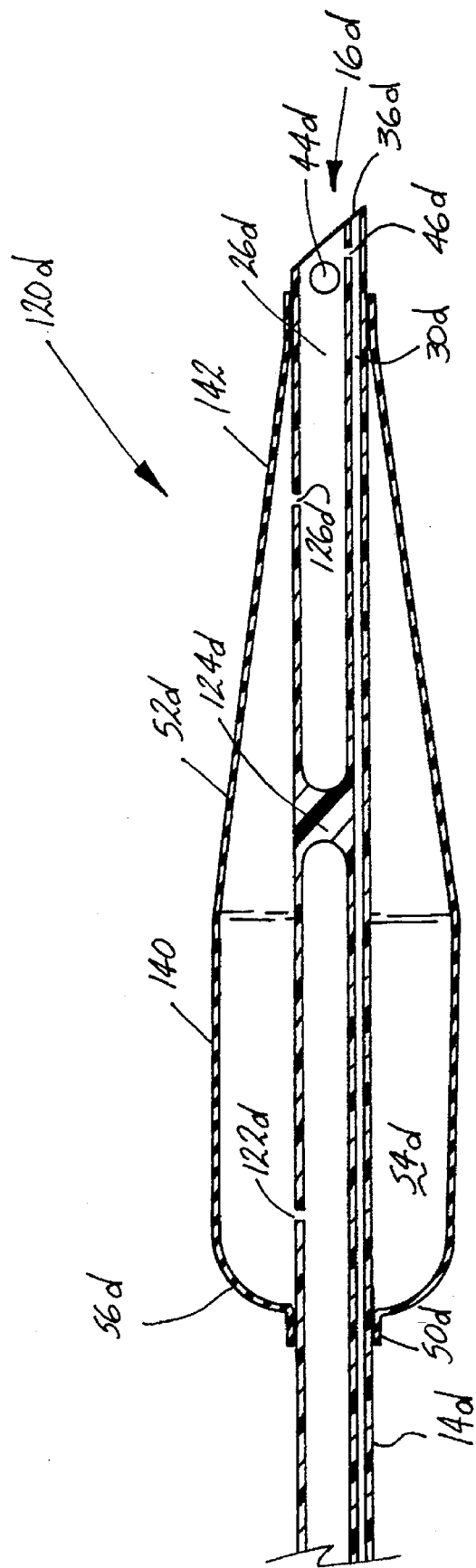
FIG. 10 is a sectional elevational view of a fifth embodiment of a catheter according to the invention, having a tapered self-inflating cuff.

In the auto-inflating cuff 120, the diameter of the cuff central section 52 remains constant over the length of the central section. Of course, when the cuff is inserted into the coronary sinus 10, it conforms to the interior dimensions thereof, as shown in FIG. 9. Alternatively, the distal end of the auto-inflating cuff can taper in the distal direction. FIG. 10 illustrate a tapered auto-inflating cuff 120d, shown apart from the coronary sinus, yet inflated to fully show its tapering shape. A proximal portion 140 of the central section 52d has a constant diameter. A distal portion 142 of the central section 52d tapers from the proximal portion 140 to the distal bond area 50d. This shape has been found to have particularly good inflation characteristics.

For consistent inflation, it is preferred to locate the exit apertures 126d as close to the distal end of the cuff 120d as practical. However, care must be taken to avoid occlusion of the exit apertures 126d by the cuff 120d, especially given the close proximity between the two at the distal end of the cuff 120d. The total liquid pressure within the cuff interior 54d is composed of two parts, the static pressure and the dynamic pressure. The dynamic pressure is a function of the velocity of the fluid flowing through the cuff interior 54d. Locating the exit aperture 126d near the center of the cuff 120d reduces any tendency of the cuff 120d to impinge against the exit aperture 126d. However, having the exit aperture 126d located away from the distal end of the cuff 120d may tend to produce an area of stagnant flow at the distal end of the cuff interior 54d. In the area of stagnant flow, the dynamic pressure is reduced, thus reducing the effectiveness of the cuff inflation. In general, multiple exit apertures 126d are provided, which greatly alleviate any such potential problems. Alternatively, a small pilot bore can be provided through the interior of the plug 124d.

More preferably, the distal bond areas 50d can be left unbonded with the catheter body 14d. In this event, the diameter of the catheter body 14d slightly exceeds the diameter of the distal bond area 50d, whereby the bond area 50d elastically and frictionally engages the catheter body 14c. Under normal operating pressures, the cuff 120d having an unbonded distal bond area 50d operates in the conventional auto-inflate fashion, with the fluid flowing into the cuff interior 50d through the entrance apertures 122d, and exiting the cuff interior 54d through the exit apertures 126d, and finally exiting the catheter 8d through the infusion lumen 26d at the catheter distal end 16d. However, if the pressure interior of the cuff 54d exceeds a predetermined value, fluid flowing through the cuff interior 54d will begin to leak pass the distal bond area 50d, in effect providing a pressure relief feature.

While particular embodiments of the invention have been shown, it will be understood, of course, that the invention is not limited thereto since modifications can be made by those skilled in the art, particular in light of the foregoing teachings. Reasonable variation and modification are possible within the foregoing disclosure of the invention without departing from the spirit of the invention. For instance, if the cuff 20 is placed upon the catheter body 14 in a state of axial compression, as opposed to the relaxed state previously discussed, the cuff 20 will have greater axial freedom when placed into the coronary sinus 10.

The embodiments of the invention in which an exclusive property or privilege is claimed are defined as follows:

1. A catheter for supplying perfusion liquid to the coronary sinus, comprising:

a tubular catheter body having an interior lumen, a proximal end, and a distal end;

an inflatable cuff on the catheter body adjacent to the distal end thereof; and a stop on the catheter body, the stop being formed of flexible material in a configuration to extend radially outwardly from the catheter body in a relaxed condition and spaced a predetermined distance proximally from the cuff, the distance being so measured that when the distal end of the catheter is inserted into the coronary sinus until the stop abuts the heart muscle surrounding the opening of the coronary sinus, the cuff will be correctly disposed within the coronary sinus.

2. A catheter according to claim 1 including a second lumen formed in the catheter body and a thread extending through the second lumen and attached to a radially outward portion of the stop to draw the stop upon application of tension to the thread into a configuration of smaller radial dimension than that of the stop in the relaxed configuration thereof.

* * * * *